(12) United States Patent
Danchin et al.

(10) Patent No.: US 7,278,999 B2
(45) Date of Patent: Oct. 9, 2007

(54) OPTHALMIC SURGERY DEVICE

(75) Inventors: Marc Danchin, Roquebrune Cap Martin (FR); Alain Brocq, Fourqueux (FR)

(73) Assignee: Promepla S.A., Principaute De Monaco (MC)

( * ) Notice: Subject to any disclaimer, the term of this patent is extended or adjusted under 35 U.S.C. 154(b) by 662 days.

(21) Appl. No.: 10/394,655

(22) Filed: Mar. 24, 2003

(65) Prior Publication Data

US 2004/0078049 A1    Apr. 22, 2004

(30) Foreign Application Priority Data

Mar. 26, 2002  (FR) .................................. 02 03782

(51) Int. Cl.
*A61F 9/00* (2006.01)
(52) U.S. Cl. ..................... 606/166; 623/905
(58) Field of Classification Search ............. 606/4–6, 606/107, 166, 167; 623/5.11, 905, 906
See application file for complete search history.

(56) References Cited

U.S. PATENT DOCUMENTS

| | | | | |
|---|---|---|---|---|
| 4,589,416 A | * | 5/1986 | Green | 606/220 |
| 5,123,905 A | * | 6/1992 | Kelman | 606/107 |
| 5,471,756 A | * | 12/1995 | Bolanos et al. | 33/501.45 |
| 5,789,911 A | * | 8/1998 | Brass | 324/72.5 |
| 5,830,233 A | * | 11/1998 | Suson et al. | 606/215 |
| RE36,693 E | * | 5/2000 | Reich | 250/507.1 |
| 6,527,115 B2 | * | 3/2003 | Rabiner et al. | 206/363 |

* cited by examiner

*Primary Examiner*—Michael J. Hayes
*Assistant Examiner*—Victor X. Nguyen
(74) *Attorney, Agent, or Firm*—Jacobson Holman PLLC

(57) ABSTRACT

The present invention relates to an ophthalmic surgery device comprising a handle presenting, at one of its ends, a first active part and, at the other of its ends, a second active part, characterized in that removable protection means are associated with at least one of the active parts.

Therefore, the functional zones of the device thus protected do not risk being altered before use.

1 Claim, 1 Drawing Sheet

OPTHALMIC SURGERY DEVICE

FIELD OF THE INVENTION

The present invention relates to an ophthalmic surgery device, also known as a "foreign body probe".

BACKGROUND OF THE INVENTION

This type of device is a precision tool comprising a handle and two active parts, located respectively at each end of said handle.

These active parts may comprise, for example, a point at one of the ends and a sort of blade of the scalpel type at the other end.

In accordance with the prior art, foreign body probes are made of metal, such as steel, in order to ensure, in particular, high precision in the details of the shapes of the active parts.

This known type of device is relatively expensive and requires a large number of pre- and post-operation treatments, such as cleaning, various verifications and sterilization.

Moreover, the different manipulations for treatment, and during transport and packaging, cause a certain wear of the active parts, and involve risks of corrosion.

Furthermore, the different manipulations as well as a treatment which is poorly carried out, may involve risks of contamination.

It is an object of the present invention to overcome the drawbacks of the prior art by proposing a inexpensive ophthalmic surgery device in which the active parts do not risk being altered.

SUMMARY OF THE INVENTION

To that end, according to the invention, the ophthalmic surgery device comprising a handle presenting at one of its ends a first active part and at the other of its ends a second active part, is characterized in that removable protection means are associated with at least one of the active parts.

According to an advantageous form of embodiment, the removable protection means comprise breakable elements presenting tongues having a recess so as to receive the corresponding active part.

The breakable elements are preferably associated with the corresponding active part by one or more point-like links adapted to be broken, and comprise a zone for gripping.

According to a particular form of embodiment, the first active part is shaped as a point while the second active part is shaped substantially as a blade.

The device is advantageously made of a thermoplastics material, such as polycarbonate.

BRIEF DESCRIPTION OF THE DRAWINGS

The invention will be more readily understood on reading the following description referring to an illustrative and non-limiting example of embodiment, with reference to the accompanying drawings, in which.

DESCRIPTION OF PREFERRED EMBODIMENT

Figure 1:
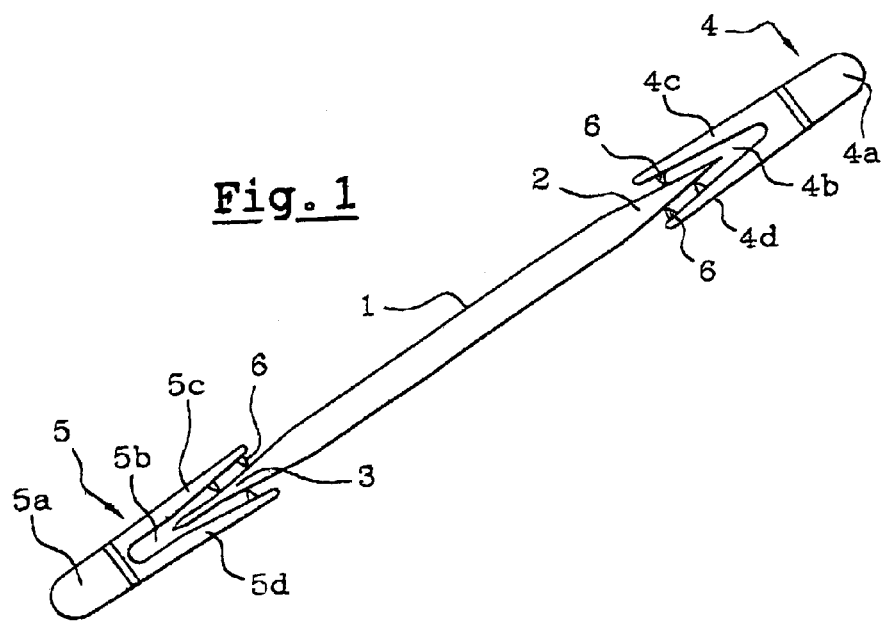
FIG. 1 is a general view of a form of embodiment of the ophthalmic surgery device according to the invention.

Referring now to the drawings, FIG. 1 illustrates a form of embodiment of the ophthalmic surgery device according to the invention.

This device, of substantially long, slim, shape, comprises a substantially cylindrical handle 1 of which each of the ends is terminated by an active part 2, 3 intended to carry out the surgical operations.

These active parts 2, 3 may take different shapes and will be described in detail hereinafter.

In order to be protected, these active parts 2, 3, are respectively associated with removable protection means 4, 5.

It will be readily understood that, even if the form of embodiment illustrated in FIG. 1 shows removable protection means 4, 5 associated with each of the active parts 2, 3, it is possible that only one of said active parts 2, 3 be associated with removable protection means 4, 5.

Each of said removable protection means 4, 5 presents the form of a breakable tongue adapted to be easily disconnected from the body of the device.

The breakable tongues 4, 5 present at their distal end, i.e. the end opposite the one associated with the corresponding active part, a substantially planar zone 4a, 5a intended to be gripped by the user's fingers with a view to disconnecting the breakable tongues 4, 5 from the body of the device.

The proximal end of the breakable tongues 4, 5 is substantially V-shaped in order to form an opening 4b, 5b respectively, whose shape is substantially complementary to the corresponding active parts 2 and 3.

Each of these active parts 2, 3 is thus protected by the breakable tongues 4, 5, by being respectively inserted in the openings 4b, 5b.

Each of the substantially V-shaped openings 4b, 5b thus forms a pair of clips 4c-4d and 5c, 5d.

Each of the clips 4c, 4d, 5c, 5d is connected to the corresponding active part 2, 3 via one or more point-like links 6 whose dimensions are sufficiently small to be able to be easily broken.

For example, in the form of embodiment of the device illustrated in FIG. 1, clip 4c is associated with the active part 2 via one point-like link 6, while clip 4d is associated with the same active part 2 via two point-like links 6.

Similarly, clip 5c is associated with the active part 3 via two point-like links 6, while clip 5d is associated with active part 3 via a single point-like link 6.

It will be understood that the dimensions of the point-like links 6, allowing the breakable tongues 4, 5 to be removably associated with the corresponding active parts 2, 3, may vary.

Similarly, said breakable tongues 4, 5 may be associated with the corresponding active parts 2, 3 via a linear link adapted nonetheless to be easily broken with a view to using the corresponding active part.

Figure 2:
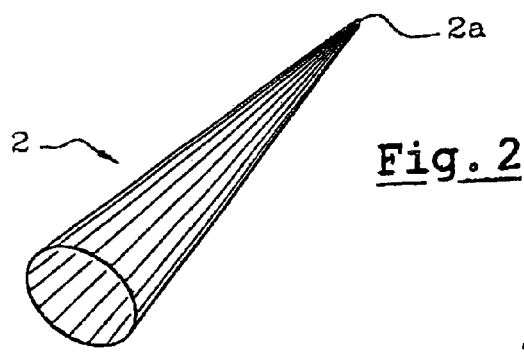
FIG. 2 is a view in detail of one of the active parts of the device according to the invention.

FIG. 2 shows a particular form of embodiment of the active part 2 in detail, on a larger scale.

This active part 2 is substantially conical in order to define a point of which the end is very fine.

Figure 3:
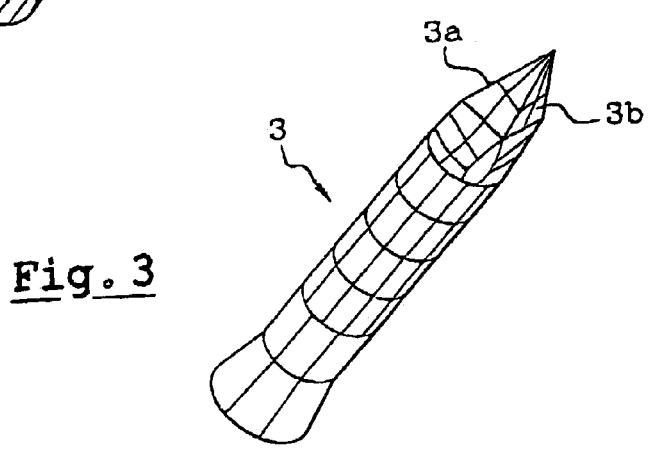
FIG. 3 is a view in detail of the other active part of the device according to the invention.

FIG. 3 shows the active part 3 in detail, on a larger scale. It is substantially cylindrical, one end 3a presenting a particular cut so as to define facets and in particular a substantially bevelled facet 3b.

Thus shaped, the active part may be used as a precision blade.

Referring again to FIG. 1, the handle 1 of the device according to the invention advantageously presents a slightly granular surface in order to facilitate grip and manipulation thereof.

In accordance with a particularly advantageous form of embodiment, the ophthalmic surgery device according to the invention is made of a thermoplastics material, enabling the whole of the device comprising the handle 1, with active parts 2, 3 at each of its ends, and the corresponding removable protection means 4, 5, to be obtained in one piece.

The thermoplastics material used may, for example, be polycarbonate.

Possible dimensions of the device are, for example, about 6 mm for the diameter of the handle 1, 130 mm for the length of the device between the two ends of the active parts 2, 3, and 175 mm for the total length of the device equipped with the breakable tongues 4, 5.

Before use, the device according to the invention is packaged so as to conserve its sterile state.

When needed, the device is removed from its protective sachet and the breakable tongue associated with the active part having to be used, is broken.

To that end, the user simply holds the device by the handle 1 and exerts an effort on the breakable tongue, for example via the gripping zones 4a, 4a.

Once the breakable tongue 4, 5 is disconnected from the corresponding active part 2, 3, said active part may be used without having to resort to prior sterilization.

In this way, the functional zones of the device according to the invention having to come into contact with the part to be operated are protected and do not risk undergoing any alteration when manipulated or packaged.

Moreover, the fact of manufacturing the device according to the invention from a thermoplastics material, such as polycarbonate, allows the device to be disposable, viz. used once only, thanks to the considerable manufacturing savings thus made.

Consequently, the pre- and post-operation treatments of the device, in the same way as the risks of contamination due to a defective treatment, such as poor sterilization, are eliminated.

What is claimed is:

1. Ophthalmic surgery device comprising
a handle presenting at one of its ends, a first active part and at the other of its ends, a second active part, each of the active parts being intended to carry out surgical operations and being associated with a removable protection means, each removable protection means being connected to the corresponding active part via one or more breakable links and having a shape of a tongue, said tongue being adapted to be disconnected from the device and being breakable, the breakable tongues having at their distal ends a substantially planar zone intended to be gripped by the user's fingers, the proximal end of each of said breakable tongues of said removable protection means being substantially V-shaped so as to form an opening whose shape is substantially complementary to the corresponding active part, wherein each of said substantially V-shaped openings forming a pair of clips.

* * * * *